United States Patent [19]
Hillberry et al.

[11] 3,932,045
[45] Jan. 13, 1976

[54] ROLLING CONTACT JOINT

[75] Inventors: Benny M. Hillberry; Allen S. Hall, Jr., both of West Lafayette, Ind.

[73] Assignee: Purdue Research Foundation, Lafayette, Ind.

[22] Filed: Mar. 5, 1973

[21] Appl. No.: 337,868

[52] U.S. Cl. .................. 403/121; 74/89; 74/22; 308/6
[51] Int. Cl.² ............ F16C 11/00; F16C 32/02; F16D 1/12; F16D 3/00
[58] Field of Search ............ 74/89.2, 89.22; 308/6; 403/121

[56] References Cited
UNITED STATES PATENTS

| | | | |
|---|---|---|---|
| 752,778 | 2/1904 | Hundhausen | 74/209 |
| 2,564,041 | 8/1951 | Vogel | 403/121 |
| 3,452,175 | 6/1969 | Wilkes | 74/798 UX |
| 3,452,309 | 6/1969 | Wilkes | 308/6 R X |
| 3,471,668 | 10/1969 | Wilkes | 308/6 R X |
| 3,640,482 | 2/1972 | Von Hippel | 242/67.1 |
| 3,643,049 | 2/1972 | Lu Conic et al. | 74/89.2 X |
| 3,739,648 | 6/1973 | Payst | 74/89.2 |
| 3,810,689 | 5/1974 | Moodie | 74/89.22 X |

OTHER PUBLICATIONS
Mechanical Engineering Magazine, Apr. 1968, pp. 11-29.

*Primary Examiner*—Werner H. Schroeder
*Assistant Examiner*—Wayne L. Shedd

[57] ABSTRACT

An apparatus is disclosed for a rolling contact joint that is particularly useful as a prosthetic joint such as a knee joint, as well as other applications requiring relatively movable sections having mechanical joints. The joint may take a variety of forms depending upon the particular situation, but in essence, includes at least two bodies that have surface portions in contact, with the bodies being movable relative to one another and constrained in this movement by the nature of the surfaces in contact and flexible straps positioned about and also in contact with the bodies. Where a basic configuration including a pair of cylinders is utilized, the flexible straps may be wrapped completely or partially around each of the cylinders to provide a joint having substantially no restraint of motion with very low friction due to the rolling contact between the contacting surfaces of the cylinders. In addition, such bodies may each have a pair of cylindrical surfaces of different diameter with respect to one another with the bodies in contact at one cylindrical surface and the flexible straps wrapped about the other of the cylindrical surfaces. If the cylindrical surfaces are concentric with respect to one another and have diameters of proper ratio, there will be no substantially resistance to the motion, and because of the rolling contact, friction will be very low. If the cylindrical surfaces are not concentric, however, then the flexible straps will be strained during rotation and a spring action will be provided in the device. Since the shape of the bodies and the positioning of the flexible straps determines the particular type of motion, various possible combinations have been described. In addition, a particular embodiment of a rolling contact joint is described for use as a prosthetic knee joint.

22 Claims, 27 Drawing Figures

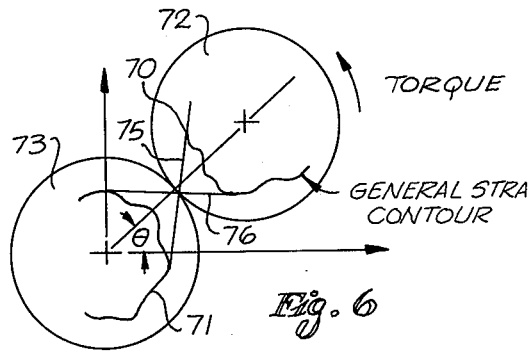
Fig. 6
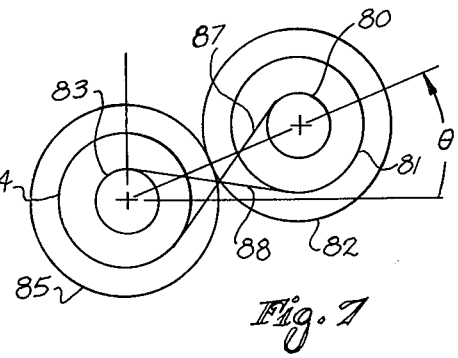
Fig. 7
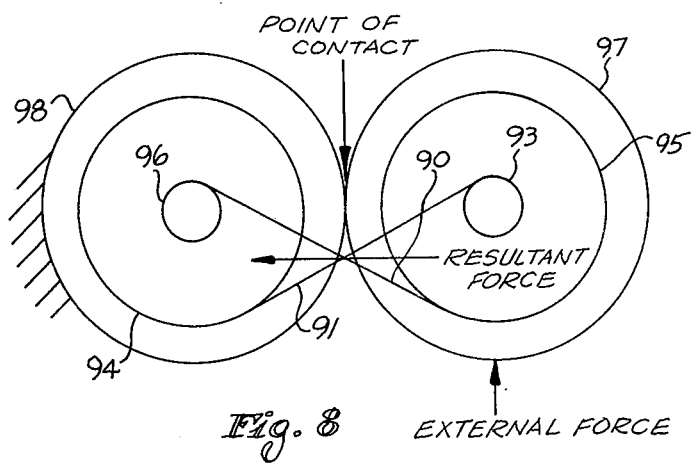
Fig. 8
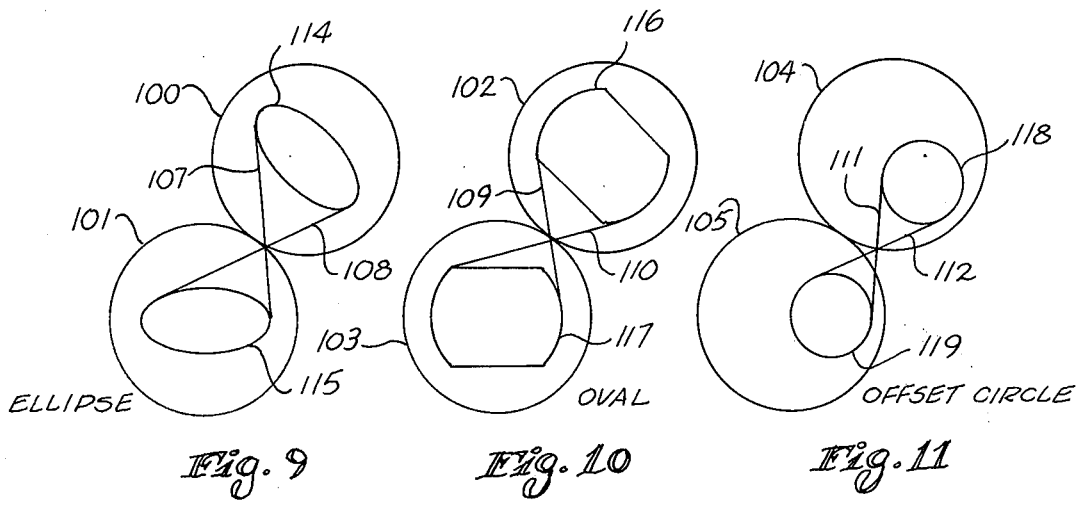
Fig. 9 ELLIPSE   Fig. 10 OVAL   Fig. 11 OFFSET CIRCLE U.S. Patent  Jan. 13, 1976  Sheet 4 of 7  3,932,045

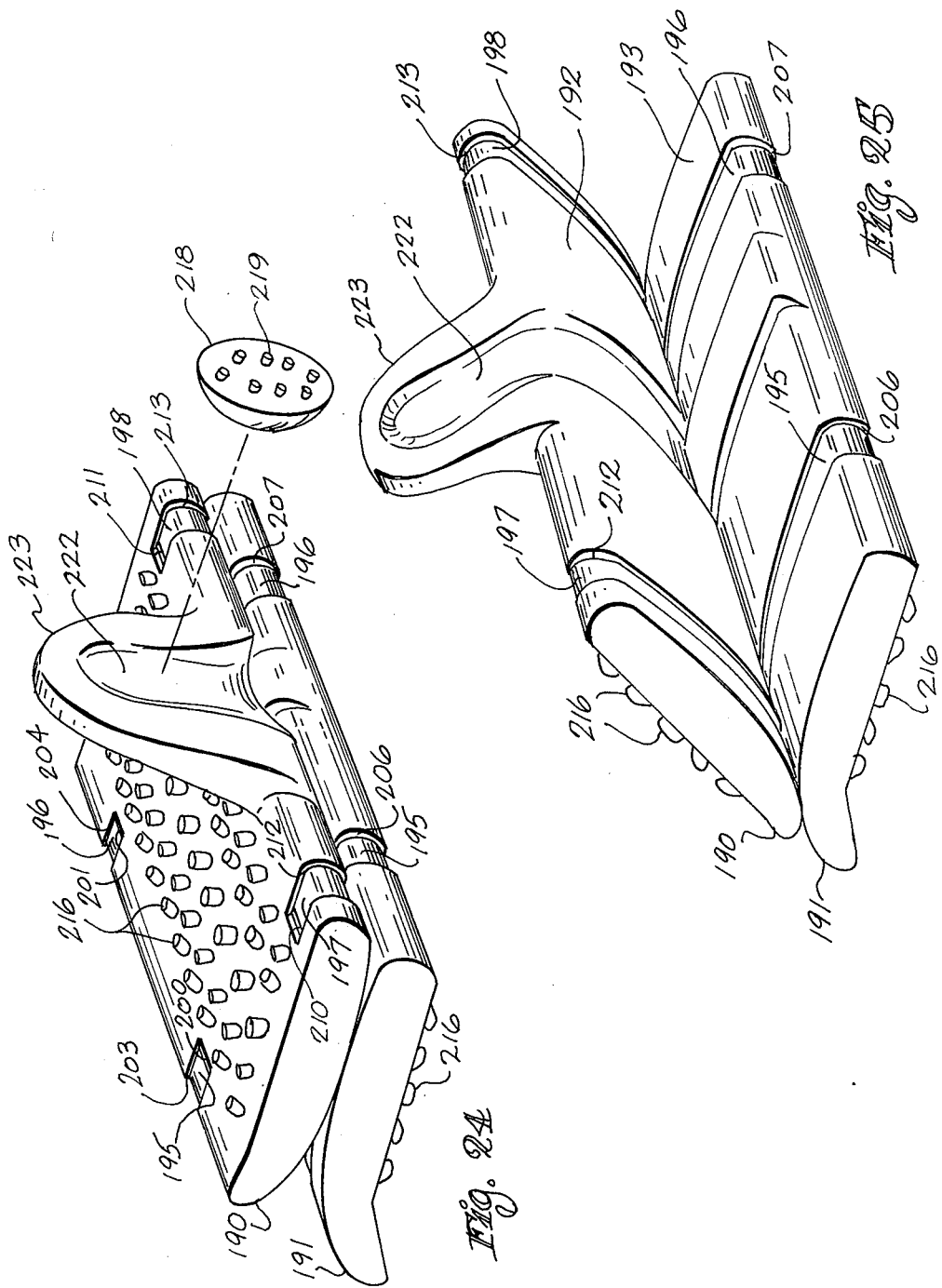

ROLLING CONTACT JOINT

BACKGROUND OF THE INVENTION

Field of the Invention

This invention relates to a rolling contact joint and, more particularly, to such a joint useful as a prosthetic knee joint.

Description of the Prior Art

Friction and wear have always been problems in conventional joint devices. In addition, such devices have not always provided satisfactory movement, particularly where the necessary movement is complicated and/or exacting, such as, for example, in at least some door hinges and in prosthetic knee joints.

While many joint devices for many different purposes have heretofore been developed and/or utilized, such devices have not been completely successful in all cases where the needed joint has to provide complicated and/or exacting movement. This is particularly true with respect to prosthetic knee joints. In the past, many hinge pin type joints have been proposed for utilization as knee joints, but such joints have met with no more than limited success due, at least in part, to an inability to provide adequate movement to come as near as possible to matching the movement afforded by the healthy human knee and/or to an inability of the joint to withstand the wear and friction resulting from sliding contact at the joint.

Recently, a roller-band device, called a "Rolamite" device, was introduced (see U.S. Pat. No. 3,572,141). This device includes two rollers inside parallel guide surfaces, the rollers being locked in a free-rolling, counterrotating cluster by the elastic constraints of an entwined flexible metallic band under tension. The geometry of this device was said to ensure that the motion of the rollers relative to the guide surfaces is accomplished by rolling and not by sliding, and the resulting device provides basically linear motion of the cluster of rollers.

While such a design as brought out hereinabove might be utilized in some joint applications, it did not completely solve problems in other joint applications, particularly prosthetic knee joint applications. Thus, the need for improved rolling contact joints usable in a variety of applications remained.

SUMMARY OF THE INVENTION

This invention provides a rolling contact joint that is well suited for use in a variety of applications and is particularly well suited for use as a prosthetic knee joint. A pair of bodies, the shape of each of which is dependent upon the particular usage contemplated, have in contact therewith a plurality of flexible straps which maintain the bodies in contact and give the resultant joint the desired action.

It is therefore an object of this invention to provide a rolling contact joint that is well suited for use in a variety of applications.

It is another object of this invention to provide a rolling contact joint that is capable of providing satisfactory movement for the use contemplated.

It is another object of this invention to provide a rolling contact joint capable of providing a predetermined action when the joint is in use.

It is still another object of this invention to provide a rolling contact joint which includes bodies which are preshaped and have flexible straps positioned thereon in a predetermined manner to achieve predetermined movement and action as desired.

It is another object of this invention to provide a rolling contact joint which includes bodies which are preshaped and have flexible straps positioned thereon in a manner to provide predetermined motion and spring action.

It is yet another object of this invention to provide a rolling contact joint that is well suited for use as a prosthetic knee joint.

It is still another object of this invention to provide an improved prosthetic knee joint that is well suited for its intended purpose.

With these and other objects in view, which shall become apparent to one skilled in the art as the description proceeds, this invention resides in the novel construction, combination, and arrangement of parts substantially as hereinafter described, and more particularly defined by the appended claims, it being understood that such changes in the precise embodiment of the hereindisclosed invention are meant to be included as come within the scope of the claims.

BRIEF DESCRIPTION OF THE DRAWINGS

The accompanying drawings illustrate at least one complete embodiment of the invention according to the best mode so far devised for the practical application of the principles thereof, and in which:

FIG. 6 shows a side view operational sketch of a rolling contact joint utilizing rollers having two cylindrical surfaces thereon, one of which is shaped in a predetermined manner and contacts flexible straps to provide a predetermined action for the joint;

FIG. 7 shows a side view operational sketch of a rolling contact joint having a plurality of cylindrical surfaces;

FIG. 8 shows a side view operational sketch of a rolling contact joint illustrating the forces present;

FIGS. 9 through 11 show side view operational sketches of rolling contact joints having alternate strap engaging surfaces;

FIG. 24 shows a perspective view of the rolling contact joint of the preferred embodiment of this invention utilized as a prosthetic knee joint;

FIG. 25 shows a perspective view of the knee joint shown in FIG. 24 with said joint in an open position;

DETAILED DESCRIPTION OF THE INVENTION

As stated hereinabove, the rolling contact joint of this invention can take many forms depending upon the particular need and/or particular requirements to be satisfied. Basically, however, a pair of bodies having engaging portions are utilized with the bodies being held together by means of flexible straps.

Figure 1:
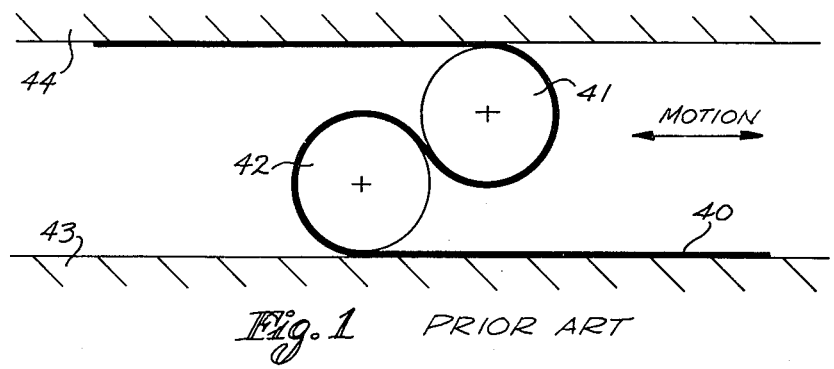
FIG. 1 shows an operational sketch of the Rolamite prior art device referred to hereinabove.

In the prior art, a system has been disclosed (see U.S. Pat. No. 3,572,141) which utilizes rollers between two guide plates. This system is shown in FIG. 1 to include a thin metallic band, or strap, 40 to suspend a pair of rollers 41 and 42 between two parallel guiding surfaces 43 and 44.

By suspending the two rollers between the guiding surfaces with the single metallic band, the device significantly decreases the bearing pressure of the rolling surfaces. This decreased bearing pressure gives the device a much improved coefficient of friction. Also, since the surfaces on the rollers always make contact with the same surfaces on the band, an additional improvement in the coefficient is achieved. It should be noted, however, that the prior art device shown in FIG. 1 is a limited-action device and therefore cannot sustain motion over a long distance.

Figure 2:
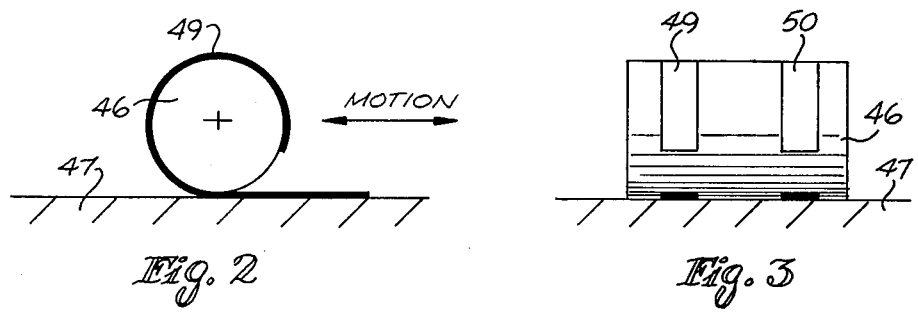
FIG. 2 shows a side view operational sketch of a rolling contact joint utilizing a single roller and a flat surface.
Figure 3:
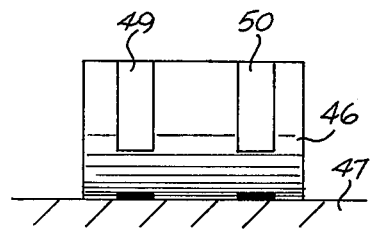
FIG. 3 shows an end view operational sketch of the rolling contact shown in FIG. 2.

As a basic consideration for the device of this invention, a new approach to rolling devices is taken using a single roller 46 and a flat surface 47, as shown in FIGS. 2 and 3. Straps 49 and 50, under a slight tension, exert no external forces or torques on the roller if the straps are in line and balanced. Straps 49 and 50 are fastened at one end to roller 46 and are wrapped therearound to pass between roller 46 and flat surface 47, the other end of the straps being fastened to flat surface 47, as indicated in FIG. 2. Using the device as shown in FIGS. 2 and 3 as a basic building block, variations can be realized.

Figure 4:
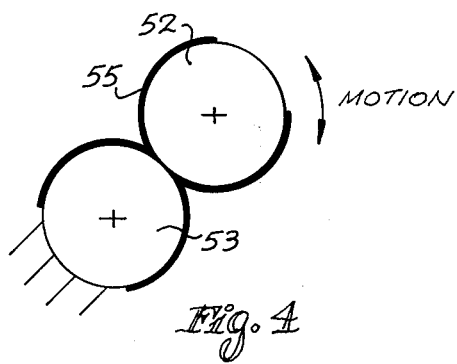
FIG. 4 shows a side view operational sketch of a rolling contact joint utilizing a fixed roller and a movable roller.

For each variation, many subsequent variations can be shown to evolve, as brought out hereinafter. As shown in FIG. 4, a moving cylinder 52 rotates about a fixed cylinder 53. Straps 55 are attached at the surface of each cylinder and extend therebetween, as shown in FIG. 4, with one end of each of straps 55 being fastened to cylinder 52 and the other end attached to cylinder 53, so that no slippage is exhibited, and therefore the rolling cylinder 52 has only rolling friction forces acting upon it.

Figure 5:
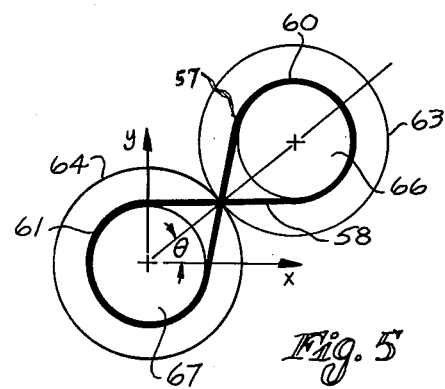
FIG. 5 shows a side view operational sketch of a rolling contact joint utilizing rollers having two cylindrical surfaces thereon.

If straps 57 and 58 are attached to an inner shoulder 60 and 61 of smaller diameter than the cylinder peripheral contact surfaces 63 and 64 of cylinder 66 and 67, as shown in FIG. 5, then the straps no longer are sandwiched between the rollers but still serve to hold the two cylinders together. As before, with no slippage and with shoulders having equally sized diameters on which the straps maintain contact, the device should not experience any impedance to motion except rolling friction.

If the contour of the strap-contacting surfaces 70 and 71 (see FIG. 6) of cylinders 72 and 73 are made noncircular of uneven diameter then the rolling cylinder 72 will, in most cases, experience a particular force and thus a torque will be required to move it. Assuming the material of straps 75 and 76 is elastic, the required torque needed to move cylinder 72 will be a function of the contour of the strap-contacting surfaces 70 and 71 and the angle theta, the general case for a rolling device requiring torque to rotate the device being shown in FIG. 6.

In order for such a rolling device to work correctly it must not slip at the point of contact. Similarly, non-circular contacting surfaces can be used to create desired motion or torque characteristics.

From a knowledge of the geometry of the contacting surfaces, the geometry of the surfaces to which the straps are attached, and the tension behavior of the straps, it is possible to analyze the torque (or spring behavior) of the device.

One example of a set of contours that offers the ability of creating torque is made of two strap-contacting shoulders 80 and 81 of cylinder 82 and shoulders 83 and 84 of cylinder 85, shoulders 80 and 84 and 81 and 83 being of different diameters as shown in FIG. 7. In this device, when the motion begins, both straps 87 and 88 unwrap from a small cylinder (shoulder 80 or 83) onto a larger cylinder (shoulder 81 or 84). This tends to stretch both of the straps 87 and 88 by an equal amount, and this stretching creates a torque which is related to the angle theta.

It might be noted that in order for a torque to exist in the rolling device, it is necessary for the resultant force between the rolling bodies, created by the straps, pass through some other point than the point of contact, as shown in FIG. 8 where straps 90 and 91 are shown fastened to strap-contacting surfaces 93 and 94 (strap 90) and surfaces 95 and 96 (strap 91) of cylinders 97 and 98.

The contours illustrated by way of example in FIGS. 9 through 11 have been analyzed with the aid of a computer. In each case a model has been built to verify the general results and to insure that there was no tendency to slip. As shown in these FIGS., cylinders 100 and 101 (FIG. 9), cylinders 102 and 103 (FIG. 10), and cylinders 104 and 105 (FIG. 11), have straps 107 and 108 (FIG. 9), 109 and 110 (FIG. 10), and 111 and 112 (FIG. 12) fastened to strap-contacting shoulders 114 and 115 (FIG. 9), 116 and 117 (FIG. 10), and 118 and 119 (FIG. 11). While the straps have been indicated and shown herein as flat bands, the strap contours can also be varied in shape to establish a desired torque-theta relationship. In addition, springs (not shown) can also be added to the rollers to create predetermined torque-theta characteristics.

Figure 12:
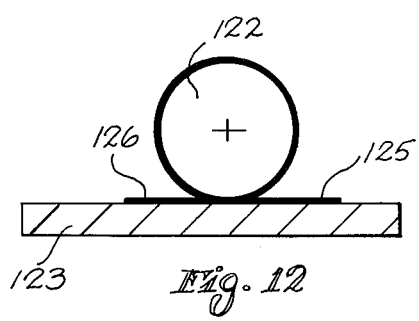
FIG. 12 shows a side view operational sketch of a roller and flat surface held in contact by a plurality of straps.
Figure 13:
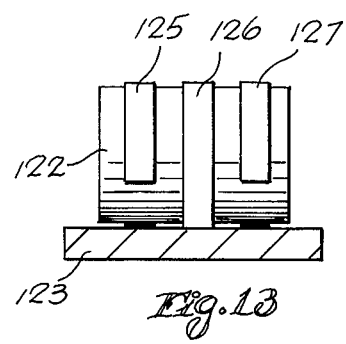
FIG. 13 shows an end view sketch of the sketch of FIG. 12.

Referring back to the general concepts discussed hereinabove, a basic building block can be established by a roller 122 on a flat surface 123, as shown in FIG. 12, said roller having a plurality of straps 125, 126 and 127 therearound, as shown in FIG. 13, with straps 125 and 127 being connected to flat surface 123 spaced from one side of roller 122 and strap 126 being connected at the other side of flat surface 123 spaced from the other side of roller 122.

Figure 14:
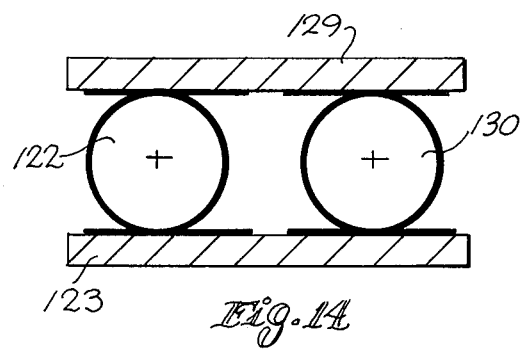
FIG. 14 shows a side view operational sketch of a plurality of rollers between flat plates.
Figure 15:
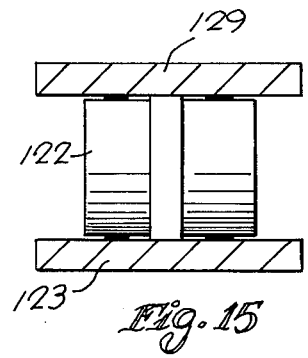
FIG. 15 shows an end view sketch of the sketch of FIG. 14.
Figure 16:
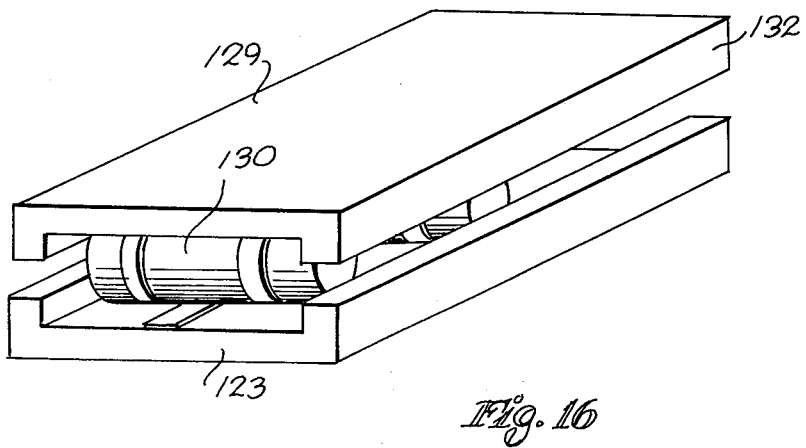
FIG. 16 shows a perspective view of a rolling linear device.

If a second flat plate 129 is attached at the top of the roller 122 in the same manner as is flat surface 123, and a second roller 130 attached to the flat surface and plate in the same manner as is roller 122 as shown in FIGS. 14 and 15 (with straps terminating at top and bottom of roller), a linear bearing is created as shown in FIG. 16 which shows a plurality of guides 132 at the edges of the top and bottom plates.

As a linear bearing such a device offers a great deal of potential. The straps allow the parts to be held tightly together and all parts meet with no relative velocity. The bearing is thought to be an improvement over conventional devices since the same points on the surfaces come into contact as the device moves back and forth.

The linear bearing can be made to exert forces as a function of position by using the techniques discussed earlier. This includes varying the width or geometry of the straps or the preset shape of the strap. It is clear that some methods would be more appropriate than others for specific purposes, as would be obvious to one skilled in the art.

Figure 17:
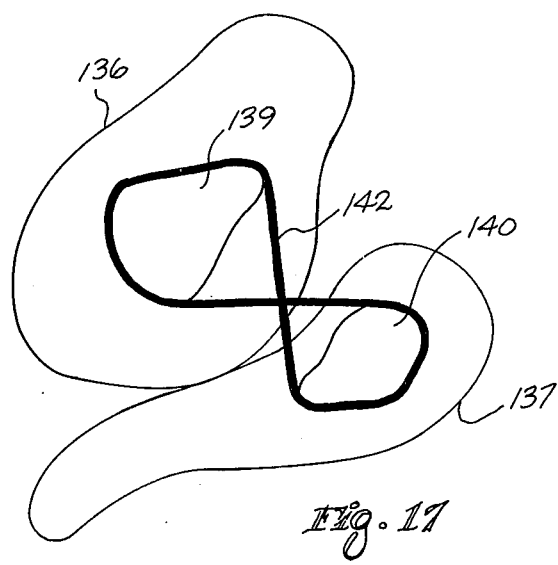
FIG. 17 shows a sketch of a rolling contact joint illustrating that no particular shape is necessary.

Referring now again to the rolling contact joint, FIG. 17 shows that no particular shape is mandatory. In other words, it is not necessary in applicants' invention that the surfaces be cylindrical, although they may be if needed for a contemplated use. As shown in FIG. 17, bodies 136 and 137 have shoulders 139 and 140 thereon, respectively, which shoulders contact strap 142 to hold the bodies in engagement.

Figure 19:
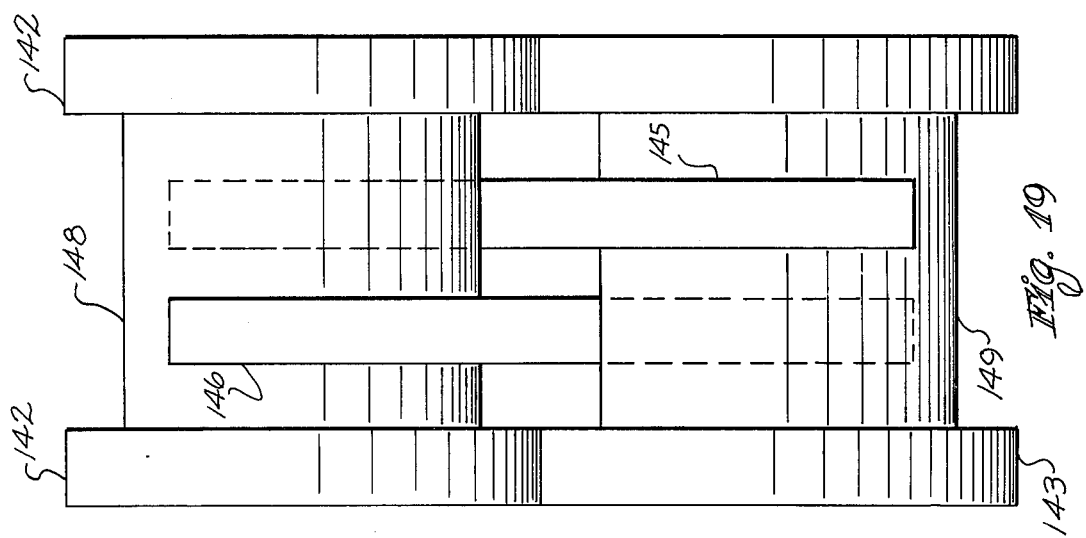
FIGS. 18 and 19 show side and end view operational sketches, respectively, of a rolling contact joint with rollers having two concentric cylindrical surfaces.
Figure 18:
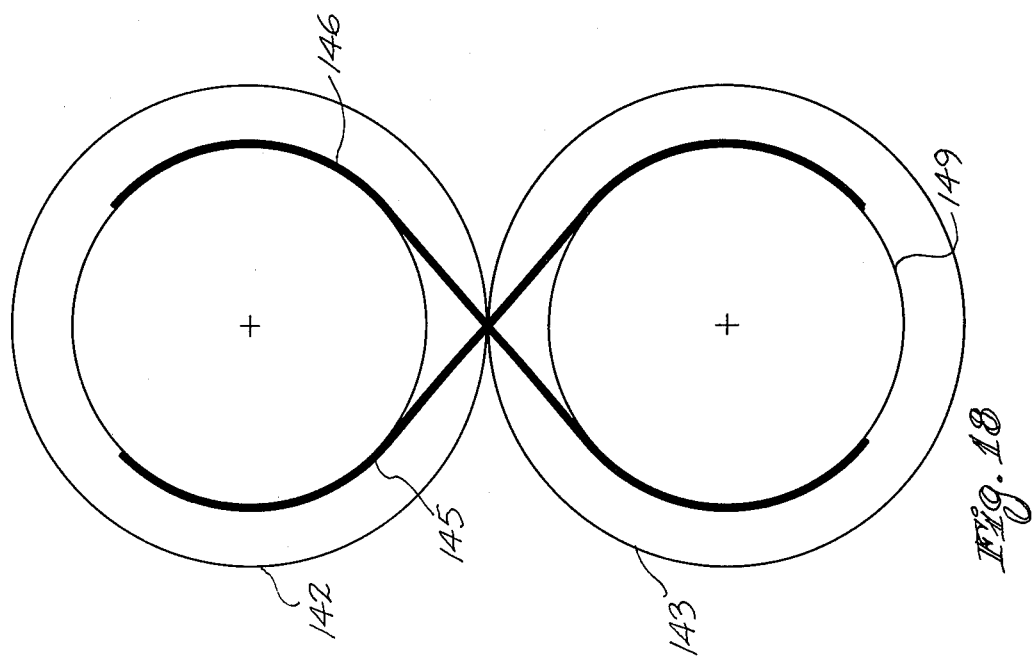

FIGS. 18 and 19 illustrate in greater detail the basic device of this invention for general use on a mechanical joint. The basic device shown in FIGS. 18 and 19 consists of two bodies 142 and 143 which move relative to each other and are constrained in their motion by either or both the contact surface between the two bodies and bands, or straps, 145 and 146 which "wind up" or "unwrap" around the two bodies by being fastened to shoulders, or smaller diameter sections, 148 and 149 of rollers 142 and 143, respectively. Portions of the surfaces of bodies 142 and 143 are in contact and held together by the bands 145 and 146 attached to the two bodies as shown in FIGS. 18 and 19. As body 142 rotates to the right with respect to body 143, band 146 wraps up on body 143 and unwraps from body 142. The opposite occurs for band 145. The reverse occurs when body 142 is rotated to the left. The constraint provided by the bands will result in pure rolling contact between the engaging surfaces of bodies 142 and 143 for certain designed contours.

Figure 20:
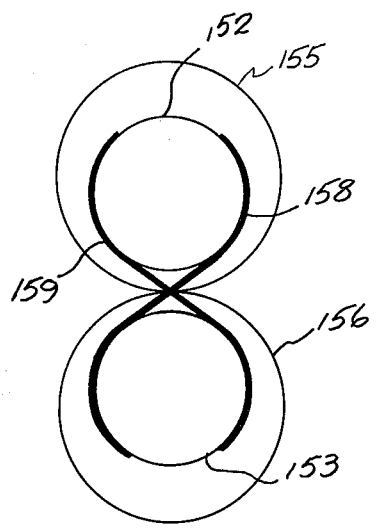
FIG. 20 shows a side view operational sketch of a rolling contact joint with rollers having strap engaging surfaces offset from the other surfaces.

Variations from the basic configuration shown in FIGS. 18 and 19 provide some very interesting combinations. If shoulder 148 is a cylinder and is concentric with the outer periphery of body 142 and shoulder 149 is concentric with the outer periphery of body 143, then rotating one body with respect to the other causes no increase or decrease in strain in the bands resulting in no restraint to the motion. Because of the rolling contact between the engaging surfaces of bodies 142 and 143, the friction will be very low. If the shoulders are not concentric with the outer periphery of the bodies, however, as shown in FIG. 20, the bands are strained during rotation providing a spring action to the device. As shown in FIG. 20, the shoulders 152 and 153 of rollers 155 and 156 are offset with respect to the outer periphery of the rollers, with straps 158 and 159 holding the rollers in engagement.

The bodies can, as brought out hereinabove, also be of different shapes to provide a particular type of motion.

Figure 21:
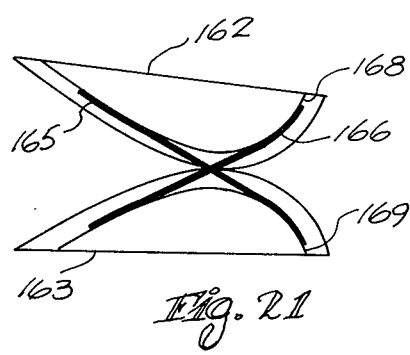
FIGS. 21 and 22 show side view operational sketches of alternate rolling contact joints.
Figure 22:
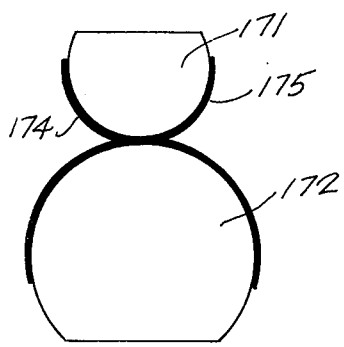

FIGS. 20, 21 and 22 illustrate three possible different combinations, with bodies 162 and 163 being held in engagement, as shown in FIG. 21 by straps 165 and 166 which are fastened to shoulders 168 and 169 of bodies 162 and 163, respectively, while, as shown in FIG. 22, bodies 171 and 172 are held in engagement by straps 174 and 175 fastened to the outer periphery of each body.

Figure 23:
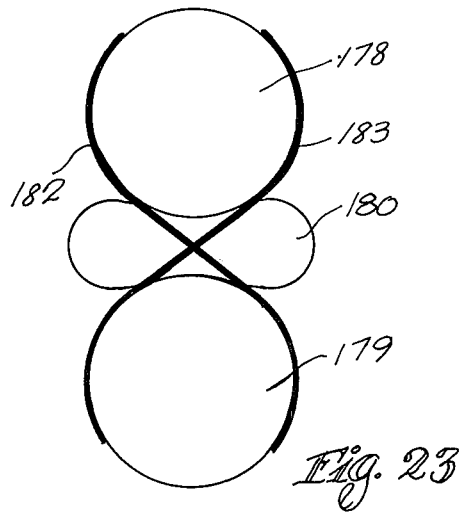
FIG. 23 shows a side view operational sketch of a rolling contact joint which includes a gas bag between rollers.

FIG. 23 illustrates a variation in which the two bodies 178 and 179 are separated with a fluid, or gas, filled bag 180, the bodies being held in engagement with the bag 180 by straps 182 and 183 fastened to bodies 178 and 179. This provides a very low friction as well as a possible cushion between the two bodies.

To summarize the advantages of the basic device, these advantages are: Possible pure rolling contact which gives low friction; freedom to obtain a particular motion; and obtaining a desired spring action to the device. There are an infinite number of variations in geometrics to obtain different performance behavior. In addition, there are infinite combinations of more than just two bodies, some of the variations being shown in FIGS. 20, 21, 22 and 23.

Figure 27:
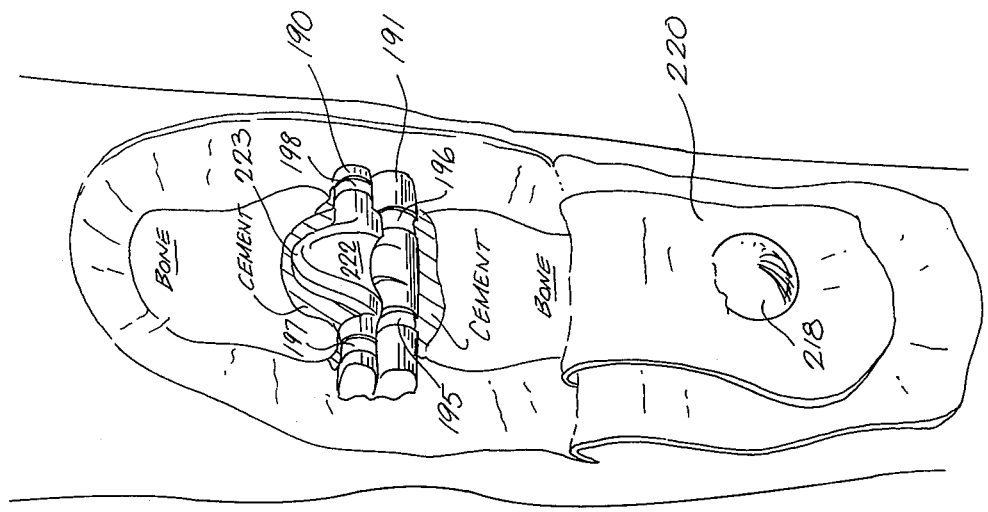
FIG. 27 shows a front partially broken away view of the knee joint shown in FIG. 26.
Figure 26:
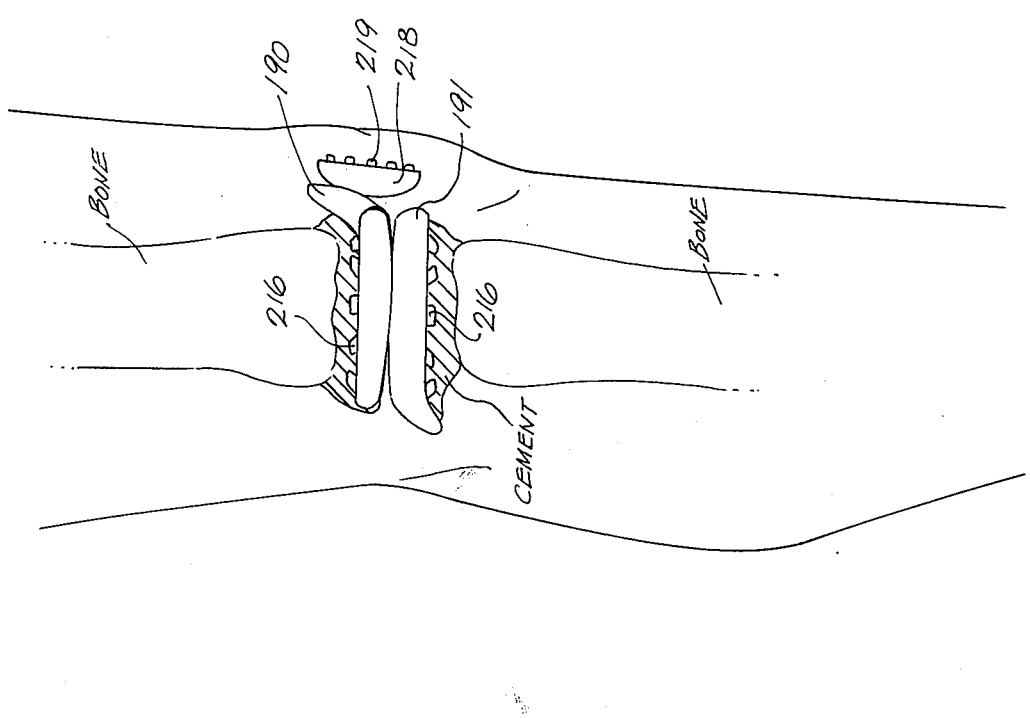
FIG. 26 shows a side partially broken away view of the knee joint of FIG. 24 implanted in a human knee for use as a prosthetic knee joint.

FIGS. 24 through 27 show a preferred embodiment of this invention utilized as a prosthetic knee joint. As shown, the knee joint device includes a femoral section, or component, 190 and a tibial section, or component, 191. The joint is implanted as a replacement for the natural hingetype knee joint, as indicated in FIGS. 26 and 27. The femoral section 190 has a curved surface 192 which rolls on surface 193 of the tibial section, as best shown in FIG. 25. The motion between the sections is constrained to rolling motion in accordance with this invention by means of a plurality of straps 195, 196, 197 and 198. Straps 195 and 196 are fastened at one end by means of pins 200 and 201 to the top portion of femoral section 190. Straps 195 and 196 extend from pins 200 and 201 respectively, over the rear edge of femoral section 190 in grooves 203 and 204, respectively, and then extend forwardly between the sections, and pass over the front edge of tibial section 191 in grooves 206 and 207, respectively, and finally are fastened at the other ends by means of pins (not shown) to the underside of tibial section 191 in the same manner as the opposite ends are fastened to femoral section 190.

In like manner, one end of straps 197 and 198 are fastened to the top portion of the femoral section (near the front thereof as shown best in FIG. 24) by means of pins 210 and 211. Straps 197 and 198 extend over the front edge of femoral section 190 in grooves 212 and 213, respectively, and then extend rearwardly between the sections and over the rear edge of the tibial section 191, the ends then being fastened to the bottom rear portion of the tibial section 191 by means of pins (not shown) in the same manner as the opposite ends are fastened to the top front portion of femoral section 190. As shown in FIGS. 24 and 25, straps 195 and 196 are spaced inwardly with respect to straps 197 and 198 so that the straps do not come into contact with one another.

Straps 195-198 provide the constraint necessary for rolling motion and hold the sections in engagement with one another. While straps have been mentioned for usage fastened to the sections by means of pins, cables could be used, if desired, and the straps or cables could be fastened in any conventional fashion. In addition, the number of straps utilized could be varied, if desired.

A plurality of protrusions 216 extend from the top side of femoral section 190 and from the bottom side of tibial section 191. These protrusions provide an interlock for the cement commonly now used in prosthetic fixation methods (see FIG. 27 where a portion of the front of the knee joint has been turned downwardly to expose the implanted knee joint).

A patella slide 218 with protrusions 219 extending outwardly therefrom attaches to the underneath side of the patella 220 and when in place (as shown in FIG. 26) rides in a groove 222 formed in the forwardly facing side of an upstanding tongue 223 of femoral section 190, the rearwardly facing portion of patella slide 218 being of convex shape to be better received in groove 222. If desired, patella slide 218 can be eliminated as could the patella groove 222 in tongue 223 of femoral section 190, at least for some applications.

The device is preferably made of stainless steel and polyethylene and the flexible members can be metal straps, rubber bands, or could be made of other materials such as leather, plastic, fabric, string or chain.

In operation, the prosthetic knee joint is surgically implanted in a human knee and thereafter performs the function of the natural knee joint. By preselecting the contours of the surfaces of the bodies (or rollers) and fastening strap positioning, the movement is made to simulate that of the natural knee as nearly as possible. By use of the device of this invention, friction and wear are also reduced so that the chances of troublefree operation over a long period of time is enhanced.

What is claimed is:

1. A rolling contact joint, comprising: a first body member having a curved external surface portion; a second body member movable relative to said first body member and having an external surface portion frictionally engaging said external surface portion of said first body member to establish a non-slipping relationship therebetween during normal operation; and flexible strap means fixed to said first and second body members to maintain said external surface portions of said body members in engagement with one another and constrained to rolling contact therebetween during said normal operation.

2. The rolling contact joint of claim 1 wherein said external surface portions of said body members have non-circular engaging shapes preselected for a particular usage.

3. The rolling contact joint of claim 1 wherein said body members are cylinders and said flexible strap means are wrapped partially about said body members and have the ends of said strap means fastened to said body members.

4. The rolling contact joint of claim 1 wherein said body members include a second external surface portion spaced from said other external surface portion, said strap means engaging said second external surface portions of said body members.

5. The rolling contact joint of claim 4 wherein said second external surface portion of each said body member is contoured to cause said joint to act in a predetermined manner.

6. The rolling contact joint of claim 4 wherein said second external portion of each of said body member is recessed with respect to said external surface portion engaging the external surface portion of said other body member.

7. The rolling contact joint of claim 4 wherein said second external portion of each said body member is offset radially with respect to the other said external portion so that a spring action is present in said joint.

8. The rolling contact joint of claim 1 wherein said first body member is a cylinder and said second body member is a flat plate, and wherein said joint further includes a second cylinder spaced from said first cylinder and a second flat plate positioned so that said cylinders are between and engaging both of said plates with said plates being substantially parallel to one another and movable relative to one another.

9. A rolling contact joint, comprising: a first body member having first and second external surface portions spaced from one another with one of said surface portions being recessed with respect to the other; a second body member having first and second external surface portions spaced from one another with one of said surface portions being recessed with respect to the other, one of said external surface portions of said first body member being in frictional engagement with one of said external surface portions of said second body member to establish a non-slip relationship therebetween during normal operation; and flexible strap means engaging the other of said external surface portions of each of said body members and maintaining said one of each of said external surface portions of said body members in constant engagement with one another whereby a rolling low friction contact is maintained between said body members during normal operation.

10. The rolling contact joint of claim 9 wherein said external surface portions of each of said first and second body members form a pair of concentric cylinders having different diameters.

11. The rolling contact joint of claim 9 wherein said external surface portions of each of said first and second body members define cylinders of different diameters, with one of said cylinders being offset with respect to the other.

12. The rolling contact joint of claim 9 wherein at least one of said first and second external surface portions of each of said first and second body members in non-circular in shape and has a differing contour so that said joint acts in a predetermined manner.

13. The rolling contact joint of claim 12 wherein said recessed external surface portion of each of said first and second body members is non-circular in shape and wherein said flexible strap means engages said recessed external surface.

14. The rolling contact joint of claim 12 wherein said external surface portion of each of said first and second body members that is not recessed is non-circular in shape and engages the like non-circular shape external surface portion of said other body member.

15. The rolling contact joint of claim 12 wherein both said first and second external surface portions of each of said first and second body members are non-circular in shape and contoured in a predetermined manner.

16. The rolling contact joint of claim 9 further including cushioning means between said body members so that said other of said external surface portions are maintained at opposite sides of said cushioning means and therefore out of contact with one another.

17. A rolling contact joint, comprising: a first body member having a curved external surface portion; a second body member having a external surface portion curved in a different direction from said first surface portion, said second surface portion frictionally engaging said curved external surface portion of said first body member and establishes a non-slipping, relatively rotatable relationship therebetween during normal operation; and flexible strap means fixed to said first and second body members and at least partially encircling the same maintaining said curved external surface portions of said body members in frictional engagement with one another and constrained to rolling contact therebetween during said normal operation.

18. The rolling contact joint of claim 17 wherein each of said first and second body members has a second external surface portion recessed with respect to said curved external surface portion, and wherein said flexible strap means are in engagement with, and at least partially encircling, said second external surface portions to maintain said curved surface portions in engagement with one another.

19. The rolling contact joint of claim 17 wherein said first and second body members are cylinders and wherein said strap means includes at least two resilient straps partially encircling different portions of said body members to maintain engagement and rolling contact between said body members regardless of the direction of rolling contact movement.

20. A rolling contact joint, comprising: a first body member having first and second curved external surface portions, said second external surface portion being recessed with respect to said first external surface portion; a second body member having third and fourth curved external surface portions, said fourth external surface portion being recessed with respect to said third external surface portion, and said first and third curved external surface portions being in frictional engagement with one another to establish a non-slipping relationship therebetween during normal operation in opposite predetermined directions; and flexible strap means including at least first and second straps engaging said second and fourth curved external surface portions of said body members, said straps being wound in opposite directions about said second and fourth external surface portions so as to at least partially encircle the same, said flexible strap means maintaining said first and third external surface portions of said body members in contact with one another to exclusively establish rolling contact therebetween during said normal operation.

21. A rolling contact joint, comprising: a first body member having first and second external surface portions spaced from one another with one of said surface portions being recessed with respect to the other; a second body member having first and second external surface portions spaced from one another with one of said surface portions being recessed with respect to the other, one of said external surface portions of said first body member being in frictional engagement with one of said external surface portions of said second body member to establish a nonslip relationship therebetween during normal operation; and flexible means engaging the other of said external surface portions of each of said body members and maintaining said one of each of said external surface portions of said body members in constant engagement with one another whereby a rolling low friction contact is maintained between said body members during normal operation.

22. The rolling contact joint of claim 21 wherein said external surface portions of said body members are curved surface portions and wherein said flexible means is a cable engaging said other of said curved external surface portions of said body members.

* * * * *